US009359414B2

(12) United States Patent
Zocevic et al.

(10) Patent No.: US 9,359,414 B2
(45) Date of Patent: Jun. 7, 2016

(54) **ANTIGENIC POLYPEPTIDES OF *TRICHINELLA* AND USES THEREOF**

(75) Inventors: Aleksandar Zocevic, Drancy (FR); Baldissera Giovani, Chatillon (FR); Sandrine A. Lacour, Alfortville (FR); Pauline Macé, Ruffec le Château (FR); Isabelle Vallée, Créteil (FR); Pascal Boireau, Bondoufle (FR)

(73) Assignee: Agence Nationale de Securite Sanitaire de l'Alimentation, de l'Environnement et du Travail, Maisons-Alfort (FR)

( * ) Notice: Subject to any disclaimer, the term of this patent is extended or adjusted under 35 U.S.C. 154(b) by 0 days.

(21) Appl. No.: 13/579,790

(22) PCT Filed: Feb. 16, 2011

(86) PCT No.: PCT/IB2011/050645

§ 371 (c)(1),
(2), (4) Date: Nov. 13, 2012

(87) PCT Pub. No.: WO2011/101790

PCT Pub. Date: Aug. 25, 2011

(65) Prior Publication Data

US 2013/0156806 A1 Jun. 20, 2013

(30) Foreign Application Priority Data

Feb. 17, 2010 (FR) ..................................... 10 00660

(51) Int. Cl.

| | |
|---|---|
| *C07K 14/435* | (2006.01) |
| *C07K 16/18* | (2006.01) |
| *G01N 33/68* | (2006.01) |
| *A61K 39/00* | (2006.01) |

(52) U.S. Cl.

CPC ....... *C07K 14/4354* (2013.01); *C07K 14/43536* (2013.01); *C07K 16/18* (2013.01); *G01N 33/6854* (2013.01); *A61K 39/00* (2013.01); *Y02P 20/582* (2015.11)

(58) Field of Classification Search

None

See application file for complete search history.

(56) References Cited

FOREIGN PATENT DOCUMENTS

| | | |
|---|---|---|
| WO | 2007/090960 | 8/2007 |
| WO | 2009/003497 | 1/2009 |

OTHER PUBLICATIONS

McGuinness et al. (Mol. Microbiol., 7:505-514, 1993).*

Moudallal et al. (EMBO Journal, 1:1005-1010, 1982).*

Abaza et al. (J. Prot. Chem., 11:433-444, 1992).*

Cruse et al., Illustrated Dict. of Immunology, 2nd ed., CRC Press, 2003, p. 46, 166, 382.*

Guiliano, Characterisation of Novel Protein Families Secreted by Muscle Stage Larvae of Trichinella Spiralis, International Journal for Parasitology, 39, pp. 515-524, 2009.

Database Uniport accession No. B6SEV3, 2008.

Database EMBL accession No. EU867516, 2008.

Wu, Identification of Antigenic Genes in Trichinella Spiralis by Immunoscreening of cDNA Libraries, Veterinary Parasitology, 159, pp. 272-275, 2009.

Mitreva, Gene Discovery in the Adenophorean Nematode Trichinella Spiralis: an Analysis of Transcription from Three Life Cycle Stages, Molecular & Biochemical Parasitology, 137, pp. 277-291, 2004.

Database Uniport accession No. B0F9S7, 2008.

Robinson Proteomic Analysis of the Excretory-Secretory Proteins of Trichinella Spiralis L1 Larva, a Nematode Parasite of Skeletal Muscle, Proteomics, 5, pp. 4525-4532, 2005.

Database EM_EST accession No. BQ542776, 2002.

* cited by examiner

*Primary Examiner* — Brian J Gangle

(74) *Attorney, Agent, or Firm* — Morgan, Lewis & Bockius LLP

(57) ABSTRACT

The invention relates to novel polypeptides which are recognized by anti-*Trichinella* antibodies. Said polypeptides can be used particularly for detecting anti-*Trichinella* antibodies and in trichinosis prevention.

5 Claims, 8 Drawing Sheets

A

```
gggtcagttttagcagcttttatcttctttttcATGGCAGTTATGCCTGAAATCAATGCG   60
                                  M  A  V  M  P  E  I  N  A    9
GATTTGAGTCCATTGGAAGAAGCCCAAAGTTACATATACCAATCTGATTTGCAAAGCGGT  120
 D  L  S  P  L  E  E  A  Q  S  Y  I  Y  Q  S  D  L  Q  S  G   29
AAAGGTCATTTCCGCAGAGTTCTCGATATAAGCGATGTCGACACAAGTGACGGATTATCC  180
 K  G  H  F  R  R  V  L  D  I  S  D  V  D  T  S  D  G  L  S   49
TTAACGATAGACGCTCTTCCAACTACATGTCCTGTGTCATCAGAAATGACTCAAGATCAA  240
 L  T  I  D  A  L  P  T  T  C  P  V  S  S  E  M  T  Q  D  Q   69
GTGTATTCAGATGAGTGCCCCGTCACCAGAGAGGAATATGACGAAATAGAATGCCATTTG  300
 V  Y  S  D  E  C  P  V  T  R  E  E  Y  D  E  I  E  C  H  L   89
AAGCTTGACCATTCTAAAACTGGCCAAATTGAATGTACATATTATGGACATtaaactatg  360
 K  L  D  H  S  K  T  G  Q  I  E  C  T  Y  Y  G  H           106
agaataaagtgatttaatgaaaaaaaaaaaaaaaaaa                         398
```

B

```
ATGTTCATCACGTTTATCTTTCTTGCTAACATACTGCTTCTTGTGCAACCATCGGAAGCA   60
 M  F  I  T  F  I  F  L  A  N  I  L  L  L  V  Q  P  S  E  A   20
TATCGTGGTCACACCAACGATGAAATTCGATTGATGGATGAGTGTAGCGATGAACCATAC  120
 Y  R  G  H  T  N  D  E  I  R  L  M  D  E  C  S  D  E  P  Y   40
ATACGAGAACACTTGGGGGAAGATGATTATATGAGTTTAATTGATGCGTGCGTTGAAGAA  180
 I  R  E  H  L  G  E  D  D  Y  M  S  L  I  D  A  C  V  E  E   60
CGACTTGGACGAAGAGTTGCAtgaagaatataagaaaagctatcaagaattgttcatttt  240
 R  L  G  R  R  V  A                                          67
caagcgacaattttatttatgaaatgaatttattgaaaatgaaatctgttacagtatt   300 cgtaataaatagctatgcagtaaaaaaaaaaaaaaaaa                        339
```

ANTIGENIC POLYPEPTIDES OF *TRICHINELLA* AND USES THEREOF

RELATED APPLICATIONS

The present application is a U.S. National Phase Application of International Application No. PCT/IB2011/050645 (filed Feb. 16, 2011) which claims priority to French Application No. 1000660 (filed Feb. 17, 2010) which are hereby incorporated by reference in their entirety.

SEQUENCE LISTING SUBMISSION VIA EFS-WEB

A computer readable text file, entitled "045636-5204_SequenceListing.txt," created on or about Aug. 17, 2012, with a file size of about 6 kb contains the sequence listing for this application and is hereby incorporated by reference in its entirety.

The present invention relates to the use of novel antigens identified in the *Trichinella* parasite in the context of the diagnosis and prevention of trichinosis.

Trichinosis is a zoonosis associated with the consumption of meat infested with the *Trichinella* parasite (MURRELL et al., Vet Parasitol, 93, 293-307, 2000).

This nematode, of the class Adenophorea, belongs to the family Trichinellidae which comprises 8 species and 3 genotypes that are related, in 2 phylogenetically distinct groups: on the one hand, the encapsulated trichinae (*T. spiralis; T. nativa; T. britovi; T. murrelli; T. nelsoni*) which infest mammals, and on the other hand, the nonencapsulated trichinae (*T. pseudospiralis; T. papuae; T. zimbabwensis*) which infest mammals, birds and reptiles (GASSER et al., Electrophoresis, 25, 3357-64, 2004). All these species can infest humans.

The biological cycle of the parasite is autoheteroxenous: it takes place entirely in the same host, which is both the intermediate host and definitive host (BOIREAU et al., Revue française des laboratoires, 71-89, 2002). The passing of the infesting larvae from one host to another is necessary in order for a new cycle to be carried out. This passage occurs through the ingestion of raw meat or barely cooked meat contaminated with larvae of the parasite. During digestion, said larvae are released, and penetrate the intestinal epithelium, where they will transform into sexual adult (Ad) worms. The fertilized females subsequently expel newborn L1 larvae (NBL) which reach the striated muscles via the lymphatic circulation and the bloodstream. These NBL larvae penetrate the muscle cells (infesting development stage L1M: L1 muscle larva), of which they bring about the dedifferentiation into nurse cells surrounded by a protective collagen capsule which is thick in the case of encapsulated trichinae, very thin in the case of nonencapsulated trichinae.

Although trichinosis is asymptomatic in animals, human infestation is reflected, during the intestinal phase, by diarrhea associated with nausea, vomiting and violent abdominal pain, while the symptoms associated with the muscle invasion phase are characterized by the combination of fever, facial edema and myalgia (CAPO & DESPOMMIER, Clin Microbiol Rev, 9, 47-54, 1996). Ocular, pulmonary, gastrointestinal, cardiac and neurological attacks can also add to this clinical picture of trichinosis, the progression of which can be lethal. The chronic nature of the infestation, marked by persistent muscle pain in patients, is associated with the survival of the parasite in the nurse cell.

The specific treatment of human trichinosis with anthelmintics is all the more effective if the diagnosis of the infestation is made early so as to allow action against all the parasitic stages and especially before the formation of the protective collagen capsule around the L1M larvae (FOURESTIE et al., Parasitol Res, 75, 36-41, 1988).

The epidemiological data have demonstrated a geographical distribution of the parasite in all parts of the world, associated with a method of transmission involving many species of the wild fauna which also maintain a domestic infestation cycle mainly represented by pigs (DUPOUY-CAMET, Vet Parasitol, 93, 191-200, 2000).

Epidemics of human trichinosis, an emerging or re-emerging zoonosis, constitute a real public health problem throughout the world owing to dietary habits and hygiene controls that are not always effective (MURRELL & POZIO, Int J Parasitol, 30, 1339-49, 2000). These epidemics essentially involve pig and wild boar meat and also horse meat (BOIREAU et al., Vet Parasitol, 93, 309-20, 2000).

The prevention of human contamination therefore involves cooking meat right through and improving rearing conditions and/or conditions for controlling animal trichinosis (pigs, horses, wild boar and other wild animal species sensitive to *Trichinella*) (BOIREAU et al., Revue française des laboratoires, 71-89, 2002).

The screening techniques for trichinosis can be divided into two categories: 1) direct detection of the L1M larvae, after artificial digestion of muscle samples, and 2) indirect detection by various immunological methods, for detecting antibodies directed against the *Trichinella* antigens.

Each of the developmental stages of the parasite, Ad, NBL and L1M, has a corresponding specific antigen profile.

It is antigen preparations derived from L1M-stage larvae which are currently used for immunodiagnosis. This is because the antigenic fractions of the two early stages Ad and NBL are difficult to purify, and it had not been possible to identify immunodominant antigens associated with one and/or the other of these two stages up until recently (LIU et al., 1-13, 2007).

Either preparations of total soluble antigen, obtained by lysis of the larvae, centrifugation of the lysate, and recovery of the supernatant, or, more commonly, excretion/secretion antigens (E/S antigens) are principally used.

The E/S antigens are produced when L1M larvae are placed under survival conditions in a culture medium; they originate from a particular organ, called the stichosome, which consists of about fifty discoid cells, the stichocytes. The stichocytes contain granules, the content of which is evacuated by a canaliculus into the lumen of the parasite's esophagus. This content, which is very highly antigenic, constitutes a part of the E/S antigens. These antigens form a complex mixture of proteins, containing in particular a group of glycoproteins (called TSL-1 antigens) bearing a specific carbohydrate molecule, known only in *Trichinella* and present in all species of this parasite, beta-tyvelose.

The preparations of E/S antigens which are currently used as a reference in terms of immunodiagnosis of trichinosis are obtained from culture medium of *T. spiralis* L1M larvae. After culture for 18 to 20 hours, the medium is recovered by filtration and then concentrated (GAMBLE et al., Vet Parasitol, 13, 349-61, 1983; GAMBLE et al., Vet Parasitol, 30, 131-7, 1988).

The principal drawback of the preparations of total soluble antigen is their lack of specificity. Antigen cross reactions with other parasitoses are commonly observed. The E/S antigens make it possible to obtain a better specificity. However, in both cases, it is difficult to produce standardized batches of antigen in large amounts.

Another problem encountered in the context of the serological diagnosis of *Trichinella* is the existence of a "blind window" of detection corresponding to the early stages of the infestation, which is reflected by false-negative serological results. This blind window can last from 3 to 8 weeks, depending on the initial infective dose. In addition, in horses, gradual disappearance of the antibodies has been observed 25 weeks after infestation.

During previous studies, the team of the inventors identified two immunodominant antigens conserved within the *Trichinella* genus and specific for said genus. These antigens are described in PCT application WO 2007/090960. One of these antigens, called NBL1 antigen, is expressed specifically at the NBL stage, while the other, called 411 antigen, appears to be common to several developmental stages of *Trichinella*.

ELISA-type serological diagnosis assays were developed on the basis of these antigens produced in the form of purified recombinant proteins. These assays allow very early serological detection of the specific anti-*Trichinella* antibodies. Comparison with a reference ELISA assay using the E/S antigens (E/S ELISA assay) made it possible to show that the ELISA assays using the NBL1 and 411 antigens can detect the presence of specific anti-*Trichinella* antibodies respectively 5 to 45 days earlier and 5 to 20 days earlier than the E/S ELISA assay. However, the humoral response targeting the NBL1 antigen then has a tendency to attenuate (on average 8 weeks after infestation), and the 411 antigen has the drawback of having a lower sensitivity than the E/S ELISA assay for detecting an infestation with *Trichinella* species other than *T. nativa*.

BRIEF DESCRIPTION OF THE DRAWINGS

FIG. 1A shows the nucleotide (SEQ ID NO: 1) and deduced amino acid (SEQ ID NO: 2) sequences of an antigen to *Trichinella* according to an embodiment of the current invention.

FIG. 1B shows the nucleotide (SEQ ID NO: 3) and deduced amino acid (SEQ ID NO: 4) sequences of an antigen to *Trichinella* according to another embodiment of the current invention

Figure 2:
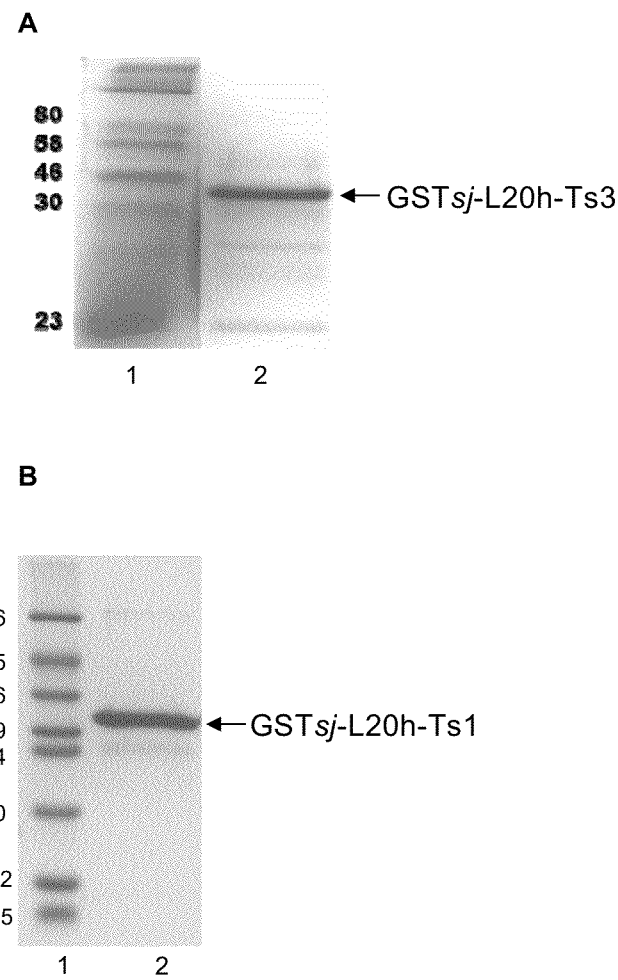
FIGS. 2A and 2B show the SDS-PAGE gels of the GSTsj-L20h-Ts3 and GSTsj-L20h-Ts1 fusion proteins.
Figure 3:
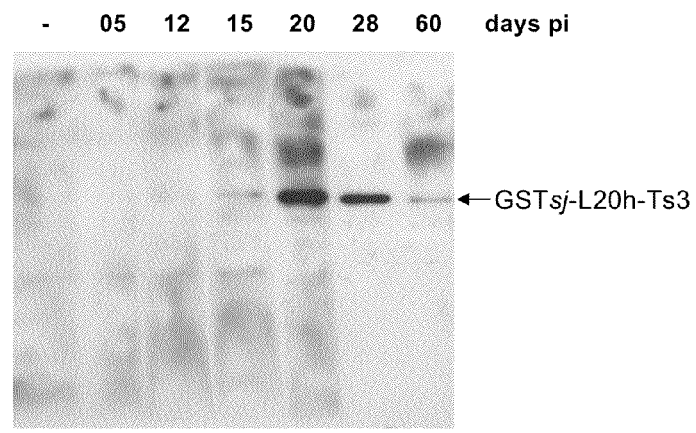
FIG. 3 shows the immunoreactivity of the recombinant L20h-Ts3 and L20h-Ts1 antigens.
Figure 4:
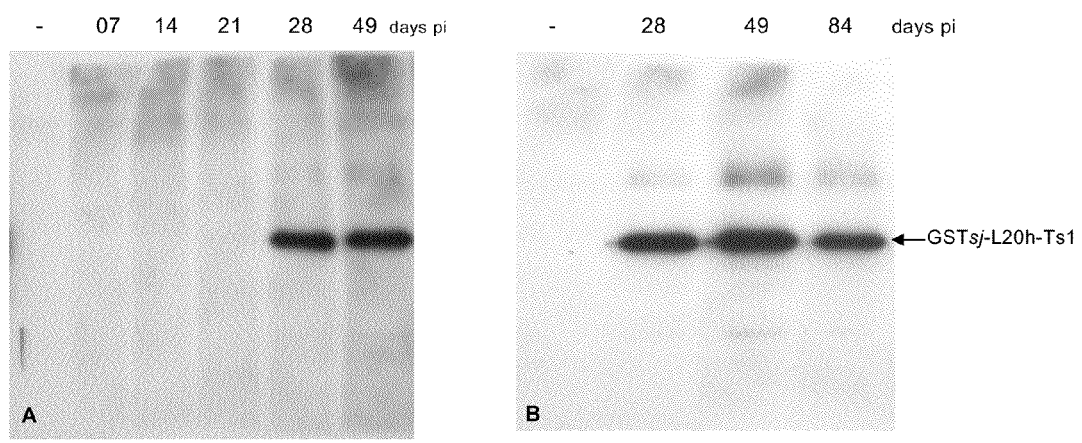
FIGS. 4A and 4B show the immunoreactivity of GSTsj-L20h-Ts1.

The inventors have now identified two new immunodominant antigens of *Trichinella*, which can be used for developing new serological diagnostic assays, or for improving the performance levels of the existing assays.

The first of these antigens is hereinafter referred to as "L20h-Ts3". The sequence of a cDNA clone encoding this antigen and the deduced polypeptide sequence are represented in FIG. 1A, and are also respectively reproduced in the appended sequence listing under numbers SEQ ID NO: 1 and SEQ ID NO: 2. The polypeptide SEQ ID NO: 2 has a high identity (91%) with the SML-3 protein (GenBank ACJ06741) recently identified among the proteins probably secreted by *T. spiralis* larvae at the muscle stage, and which could play a role in the formation of the nurse cell (GUILIANO et al., Int J Parasitol, 39, 515-24, 2009); however, the antigenic properties of the SML-3 protein have not been studied to date.

The second antigen is hereinafter referred to as "L20h-Ts1". The sequence of a cDNA clone encoding this antigen and the deduced polypeptide sequence are represented in FIG. 1B, and are also respectively reproduced in the appended sequence listing under numbers SEQ ID NO: 3 and SEQ ID NO: 4. The polypeptide SEQ ID NO: 4 does not possess any identity with any known protein of *Trichinella* or of other organisms.

The L20h-Ts3 and L20h-Ts1 polypeptides, produced in recombinant form, make it possible to detect, at an early stage, the humoral response directed against *Trichinella*. In addition, the humoral response targeting these antigens persists for longer after infestation than in the case of the recombinant NBL1 antigen, where it begins to attenuate approximately 8 weeks after infestation. The use of the L20h-Ts3 and L20h-Ts1 polypeptides therefore makes it possible to broaden the time window for detection of the humoral response.

Consequently, the subject of the present invention is the use of an antigenic polypeptide recognized by anti-*Trichinella* antibodies, as a reagent for detecting anti-*Trichinella* antibodies in a biological specimen, characterized in that said polypeptide is chosen from:

a) a polypeptide comprising the sequence SEQ ID NO: 2, or comprising a sequence exhibiting at least 70%, and by order of increasing preference, at least 75%, 80%, 85%, 90% or 95%, identity with the sequence SEQ ID NO: 2;

b) a polypeptide comprising amino acids 21-67 of the sequence SEQ ID NO: 4 (which represent the mature form of the L20h-Ts1 protein), or comprising a sequence exhibiting at least 70%, and by order of increasing preference, at least 75%, 80%, 85%, 90% or 95%, identity with the sequence of amino acids 21-67 of the sequence SEQ ID NO: 4.

Advantageously, in the context of the implementation of the present invention, it is possible to use a mixture, comprising a polypeptide a) and a polypeptide b) as defined above, or else a mixture comprising a polypeptide a) and/or a polypeptide b) as defined above, combined with one or more other antigenic polypeptide(s) recognized by anti-*Trichinella* antibodies, for example one or more of the polypeptides derived from the NBL1 and 411 antigens, described in PCT application WO 2007/090960.

The subject of the present invention is more particularly a method for detecting the presence of anti-*Trichinella* antibodies in a biological sample, said method being characterized in that it comprises:

- bringing said biological sample into contact with a polypeptide a) and/or a polypeptide b), as defined above, under conditions which allow the formation of an antigen/antibody complex between said polypeptide(s) and the anti-*Trichinella* antibodies possibly present in said sample;
- detecting, by any appropriate means, the antigen/antibody complex possibly formed.

Generally, said biological specimen is a serum specimen. It can be obtained from any individual (mammal, bird or reptile) belonging to a species that can be infested with *Trichinella*, and in which it is desired to detect the presence of this parasite. Advantageously, it is a specimen obtained from a mammal, for example from a livestock animal, or from a human patient.

This combination makes it possible in particular to broaden the spectrum of reactivity, and also the time window for detection of the humoral response, compared with each of the polypeptides used individually.

The polypeptide b) defined above is also part, as such, of the subject of the present invention.

The present invention encompasses in particular chimeric polypeptides comprising one or more copies of a polypeptide a) and/or one or more copies of a polypeptide b) as defined above, optionally fused to one or more heterologous polypeptide(s), for example one or more polypeptides derived from the NBL1 and 411 antigens described in PCT application WO 2007/090960.

The subject of the present invention is also the polynucleotides encoding the polypeptide b) or encoding a chimeric polypeptide in accordance with the invention, and also recombinant vectors comprising said polynucleotides, and host cells transformed with said vectors.

The subject of the present invention is also a composition comprising a polypeptide a) and a polypeptide b) as defined above, or comprising a polypeptide a) and/or a polypeptide b) as defined above, combined with one or more other antigenic polypeptide(s) recognized by anti-*Trichinella* antibodies, for example one or more of the polypeptides derived from the NBL1 and 411 antigens described in PCT application WO 2007/090960.

The polypeptides a) and b) defined above can be used in the context of various methods for detecting antibodies, which are known in themselves. By way of examples, mention may in particular be made of methods of ELISA type (direct, indirect or sandwich), methods of microagglutination on beads, and also methods of electrophoretic transfer coupled with immunolabeling.

The subject of the present invention is also a kit for detecting the presence of anti-*Trichinella* antibodies in a biological sample, characterized in that it comprises a polypeptide a) and/or a polypeptide b) as defined above, and, where appropriate, buffers and reagents suitable for making up a reaction medium which allows the formation of an antigen/antibody complex, and, optionally, means for detecting said antigen/antibody complex. Optionally, it may comprise one or more other antigenic polypeptides recognized by anti-*Trichinella* antibodies, for example one or more of the polypeptides derived from the NBL1 and 411 antigens described in PCT application WO 2007/090960.

Advantageously, said polypeptide(s) is (are) immobilized on a solid support. By way of nonlimiting examples of solid supports that can be used, mention will be made of microtitration plates, beads, microbeads or microparticles, strips, etc.

Said kit may also comprise reference samples, such as one or more negative serum or sera and one or more positive serum or sera.

The subject of the present invention is also the use of a polypeptide b), as defined above, for preparing an antibody specifically directed against said polypeptide.

These polypeptides can be used in the context of various methods, known in themselves, for preparing antibodies. They may for example (optionally after addition of a suitable adjuvant) be used for immunizing an animal. They may also be grafted onto an affinity chromatography support, in order to make it possible to purify, from a biological fluid, the antibodies specifically directed against the polypeptide concerned. The biological fluid may, for example, be the serum of an animal previously immunized with the polypeptide concerned, or a hybridoma supernatant; it may also be the serum of an animal infested with *Trichinella* from which it is desired to isolate a sub-population of antibodies specifically directed against the polypeptide concerned.

The present invention also encompasses any antibodies specifically directed against a polypeptide b) as defined above. This may involve polyclonal antibodies or monoclonal antibodies.

Antibodies specifically directed against a polypeptide can be obtained by various techniques known in themselves, and in particular by the conventional methods comprising the immunization of an animal with the polypeptide concerned (to which a suitable adjuvant has optionally been added), and the recovery of its serum (for the production of polyclonal antibodies) or of its lymphocyte cells (for the production of monoclonal antibodies).

The polypeptides a) and b) defined above, and also the polynucleotides encoding these polypeptides, can be used for preparing immunogenic compositions, and in particular anti-*Trichinella* vaccines.

The subject of the present invention is also an immunogenic composition comprising one or more polypeptide(s) a) and/or one or more polypeptide(s) b) as defined above, or one or more polynucleotide(s) encoding said polypeptide(s), combined with one or more adjuvant(s) for enhancing the immune response. Optionally, said composition may comprise one or more other immunogenic polypeptide(s) recognized by anti-*Trichinella* antibodies, for example one or more of the polypeptides derived from the NBL1 and 411 antigens described in PCT application WO 2007/090960.

According to one preferred embodiment of an immunogenic composition in accordance with the invention, it is a vaccine.

A large variety of adjuvants which make it possible to increase the immunogenicity of peptides are known in themselves to those skilled in the art: by way of examples of adjuvants, mention will be made of alum (aluminum hydroxide), complete Freund's adjuvant or incomplete Freund's adjuvant (IFA), liposomes, and also virosomes (reconstituted viral envelopes), peptide derivatives of muramic acid, etc. In the case of a vaccine a pharmacologically acceptable adjuvant will of course be chosen; by way of examples of preferred adjuvants, mention will be made of adjuvants of "oil-in-water" emulsion type, for example the adjuvants sold by the company SEPPIC under the names MONTANIDE ISA 70 and MONTANIDE ISA 775, and which are also described in patents EP 480 982, EP 825 875, U.S. Pat. No. 5,422,109, U.S. Pat. No. 6,251,407 and U.S. Pat. No. 6,610,309.

Where appropriate, in particular in the case of short peptides (<30 amino acids), said polypeptide(s) can be coupled to a carrier protein.

By way of examples of carrier proteins, mention will in particular be made of KLH (keyhole limpet hemocyanin), bovine serum albumin (BSA), ovalbumin, tetanus toxoid or diphtheria toxoid. It is also possible to form a multiepitope composition, by combining several copies of the same peptide with one another, and optionally with other peptide epitopes, in the form of chimeric polypeptides, or by means of a polymeric chain, for example a polylysine.

If a polynucleotide is used as immunogen, the immunogenic composition may be in the form of a recombinant vector into which the polynucleotide(s) to be administered is (are) inserted. Use may be made, for example, of the viral vectors such as poxviruses, adenoviruses, retroviruses, lentiviruses, herpesviruses and AAVs (adeno-associated viruses), etc. It can also be in the form of a nonpathogenic bacterium transformed with one or more expression vectors containing said polynucleotide(s). It is also possible to administer the polynucleotide(s) directly, in the form of naked DNA, or to incorporate it (them) into liposomes. In the case of a vaccine, use will preferably be made of a non-pathogenic bacterium (for example a *lactobacillus*, or a nonpathogenic strain of *Escherichia coli* or *Salmonella suis*), or a vector derived from a vaccine viral strain; for example a vector derived from a vaccine strain of the pseudorabies (Aujeszky's disease) virus.

The present invention will be understood more clearly from the further description which follows, which refers to examples illustrating the use of the L20h-Ts3 and L20h-Ts1 antigens for immunodiagnosis of trichinosis.

EXAMPLE 1

Identification of the L20h-Ts3 and L20h-Ts1 Antigens, and Production of these Antigens in the Form of Recombinant Proteins in a Prokaryotic Expression System An immunoscreening of cDNA expression libraries of the early stages of *Trichinella* (14 h, 20 h, 48 h after infection of mice) was effected with sera and intestinal mucosa culture supernatants of pigs experimentally infested with *T. spiralis*.

The L20h-Ts3 gene was identified in 41 of the clones of the cDNA libraries obtained 14 h and 20 h after infection of the mice. The nucleotide sequence (SEQ ID NO: 1) and the deduced polypeptide sequence (SEQ ID NO: 2) of one of these clones are represented in FIG. 1A.

Its length is 398 bp, including the 33 bp of 3'UTR, a putative polyadenylation signal (underlined in FIG. 1A), and an open reading frame encoding a protein of 106 aa, with a molecular weight of 11906.0 Da and an isoelectric point of 4.21. No peptide signal was identified on the basis of the algorithm of BENDTSEN et al. (BENDTSEN et al., J Mol Biol, 340, 783-95, 2004). The search for homologs in the databases reveals a strong identity (91%) between the deduced polypeptide sequence of L20h-Ts3 and a protein of *T. spiralis*, called SML-3 (GUILIANO et al., Int J Parasitol, 39, 515-24, 2009).

This clone was digested with BamHI-NotI (New England BioLabs, Beverly, Mass.), and the restriction fragment containing the complete coding sequence of L20h-Ts3 was subcloned into the pGEX-6P-1 vector (GenBank U78872). This vector has an N-terminal *Schistosoma japonicum* glutathione S-transferase tag (GSTsj) (the GSTsj exhibits no immunological cross reactions with *Trichinella*). The resulting expression vector, called pGEX-6P-1-(L20h-Ts3), encodes a recombinant protein containing the whole of the L20h-Ts3 sequence and bearing a GSTsj tag in the N-terminal position and a polyhistidine tag in the C-terminal position.

The L20h-Ts1 gene was identified in 121 of the clones of the cDNA libraries obtained 20 h and 48 h after infection of the mice. The sequence (SEQ ID NO: 3) of one of these clones is represented in FIG. 1B. Its length is 339 bp, including 139 bp of 3'UTR, a putative polyadenylation signal (underlined in FIG. 1B), and an open reading frame encoding a protein of 67 aa (SEQ ID NO: 4), with a molecular weight of 7834.9 Da and an isoelectric point of 4.42. A signal peptide of 20 aa (in bold in FIG. 1B) was identified on the basis of the algorithm of BENDTSEN et al. (2004). The search for homologs in the databases revealed no homology with known *Trichinella* proteins.

This clone was digested with BamHI-NotI (New England BioLabs, Beverly, Mass.), and a restriction fragment encoding the $Tyr_{21}$-$Ala_{67}$ fragment of L20h-Ts1 (corresponding to the mature form, without the signal peptide) was subcloned into the pGEX-6P-1 vector. The resulting expression vector, called pGEX-6P-1-(L20h-Ts1), encodes a recombinant protein containing the sequence of the mature form of L20h-Ts1 and bearing a GSTsj tag in the N-terminal position and a polyhistidine tag in the C-terminal position.

The pGEX-6P-1-(L20h-Ts3) or pGEX-6P-1-(L20h-Ts1) vector was used to transform *E. coli* bacteria (BL21 strain), and the expression of each recombinant protein (containing an N-Ter GSTsj tag or a C-Ter histidine tag) was induced by adding 0.5 mM (final concentration) of isopropyl-β-D-thiogalactopyranoside (IPTG) and incubating for 3 h, at 37° C. and 225 rpm. The bacteria induced were centrifuged (4000×g, 20 min at 4° C.), resuspended in lysis buffer (20 mM Tris-HCl, pH 8.0; 150 mM NaCl) supplemented with 0.5 mg/mL of lysozyme, and lyzed by means of three freezing/thawing cycles in liquid nitrogen.

Next, 5 μg/mL of DNase I were added to the lysate incubated for 15 min at 37° C. The lysate was then incubated for 1 h 30 at 4° C. on a rotary shaker in a 50 mL conical-bottom Falcon® tube (Becton Dickinson, Le Pont-De-Claix, France) in the presence of an Ni-NTA matrix (GE Healthcare Europe, Orsay, France) preequilibrated in lysis buffer. The lysate-matrix mixture was loaded onto a PD-10 column (GE Healthcare Europe, Orsay, France) in order to remove the unbound proteins or the contaminants, and then transferred into a new 50 mL Falcon® tube and washed with 50 mL of washing buffer I (20 mM Tris-HCl, pH 8.0; 300 mM NaCl) for 30 min at 4° C. on a rotary shaker. After centrifugation for 5 min (1500×g, 4° C.), the mixture was washed 4 times with 50 mL of washing buffer II (20 mM Tris-HCl, pH 8.0; 300 mM NaCl; 30 mM imidazole) for 30 min at 4° C.; these washes were followed by a final centrifugation for 5 min (1500×g, 4° C.). Finally, each recombinant protein was eluted with the elution buffer (20 mM Tris-HCl, pH 8.0; 300 mM NaCl; 500 mM imidazole) and the concentration was determined using a spectrophotometer at 280 nm. The recombinant protein was divided up into aliquot fractions and stored at −20° C. in 10% glycerol.

The denaturing electrophoresis (SDS-PAGE) gels of the GSTsj-L20h-Ts3 and GSTsj-L20h-Ts1 fusion proteins are respectively represented in FIGS. 2A and 2B (lane 1: molecular weight markers). On these gels, the GSTsj-L20h-Ts3 and GSTsj-L20h-Ts1 proteins both appear in the form of a single band at the expected size for the fusion protein.

EXAMPLE 2

Immunoreactivity of the L20h-Ts3 and L20h-Ts1 Proteins in Western Blotting

Anti-*Trichinella* Sera

Specific Pathogen Free pigs (SPF pigs) or pigs from a conventional farm were infested with 200, 1000, 20 000 infesting larvae of *T. spiralis* (ISS004, International *Trichinella* Reference Centre, Rome, Italy) or of *T. britovi* (ISS100). Blood samples were taken 48 h before infestation (negative control) and at 5, 10, 15, 20, 25, 30, 40, 50 and 60 days post-infestation (pi).

Sera originating from SPF pigs infested with 20 000 L1M larvae of *T. spiralis* (ISS003) or *T. britovi* (ISS002) were also used. Blood samples were taken 24 h before infestation (negative control) and at 1, 2, 3, 4, 5, 6, 7, 8, 12, 16, 20 and 25 weeks pi.

Sera of pigs originating from indoor-production factory farms in Ille-et-Vilaine (France), and tested negative for trichinosis by artificial digestion, were collected in 2004 and were used as negative reference sera.

Western Blotting

The immunoreactivity of the recombinant L20h-Ts3 and L20h-Ts1 antigens (in the form of the GSTsj-L20h-Ts3 and GSTsj-L20h-Ts1 fusion proteins) was analyzed by Western blotting.

The recombinant proteins were subjected to electrophoresis under denaturing conditions (15% SDS-PAGE, 700 ng of protein per Well), and blotted onto a nitrocellulose membrane. After blocking of the membranes by incubation overnight at 4° C. in PBS buffer containing 0.1% TWEEN 20 (Polysorbate 20) (PBS-T) and 5% skimmed milk, they were washed 3 times in PBS-T for 5 min. The membranes were then incubated for 1 h at ambient temperature with:

in the case of L20h-Ts3, sera from SPF pigs experimentally infested with 20 000 L1M larvae of *T. spiralis*, collected at −2, 5, 12, 15, 20, 28 and 60 days after infestation and diluted to 1/300 in PBS-T containing 5% skimmed milk, in the case of L20h-Ts1, the serum of an SPF pig experimentally infested with 20 000 L1M larvae of *T. spiralis*, collected at −1, 7, 14, 21, 28, 49 and 84 days after infestation and diluted to 1/300 in PBS-T containing 5% skimmed milk.

After 3 washes for 5 min in PBS-T, the membranes were incubated for 1 h at ambient temperature with a rabbit anti-pig IgG secondary antibody labeled with peroxidase, diluted to 1/10 000. After 3 further washes, visualization was performed by means of the "ECL PLUS WESTERN BLOTTING AND AMERSHAM HYPERFILM ECL" kit (GE Healthcare Europe, Orsay, France).

L20h-Ts3:

The results obtained with the sera of SPF pigs experimentally infested with 20 000 L1M larvae of *T. spiralis* and collected at −2, 5, 12, 15, 20, 28 and 60 days pi are illustrated by FIG. 3. These results show that the recombinant L20h-Ts3 antigen (GSTsj-L20h-Ts3) is clearly recognized from 20 days pi (a weak band is visible from 15 days pi onward), and at least up to 60 days pi.

L20h-Ts1:

The results are illustrated by FIG. 4. These results show that the recombinant L20h-Ts1 antigen (GSTsj-L20h-Ts1) is clearly recognized from 28 days pi (a weak band is visible from 21 days pi onward), and at least up to 84 days pi by the serum of an SPF pig experimentally infested with 20 000 L1M larvae of *T. spiralis* (FIGS. 4A and 4B) (It should be noted that detection at 112 days pi was also possible with another SPF pig experimentally infested with 20 000 L1M larvae of *T. spiralis*, data not shown). The recombinant L20h-Ts1 antigen (GSTsj-L20h-Ts1) is also recognized (a weak band is visible) at 60 days pi in the case of a pig infested with 200 L1M larvae of *T. spiralis* (data not shown).

EXAMPLE 3

Immunoreactivity of the Recombinant L20h-Ts3 Antigen in Indirect ELISA

The immunoreactivity of the recombinant L20h-Ts3 antigen was evaluated by indirect ELISA, in comparison with the E/S antigen of *T. spiralis*, and with the NBL1 antigen described in PCT application WO 2007/090960.

The sera from pigs infested with *Trichinella* that are used are those described in Example 2 above. A total of 220 negative pig reference sera were used for determining the diagnostic threshold.

The E/S antigen used as reference is that of the ELISA assay sold by the Pourquier Institute (Montpellier, France).

The protocol used for the ELISA assays is the following: 100 μL/well of antigen diluted in sensitizing buffer (12 mM sodium carbonate; 35 mM sodium bicarbonate, pH 9.6) were deposited and incubated for 2 h at 37° C. in a microtitration plate (Immuno 96 MicroWell Plates F96 MaxiSorp, Nunc, Roskil, Denmark). Next, each well was washed 5 times with 2504 of washing buffer (distilled water, 0.05% TWEEN 20 (Polysorbate 20)) and incubated for 30 min at 37° C. with 2004 of saturation buffer (PBS, 1% gelatin; 0.05% TWEEN 20 (Polysorbate 20)). After 5 washes with the washing solution, 200 μL/well of primary antibodies (sera) diluted in saturation buffer were deposited and incubated for 1 h at 37° C. After 5 washes with the washing solution, 100 μL/well of rabbit anti-pig IgG secondary antibodies conjugated to peroxidase (diluted to 1/50 000 in saturation buffer) were deposited and incubated for 1 h at 37° C. Finally, the wells were washed 5 times with the washing solution, and 100 μL/well of 3,3',5,5'-tetramethylbenzidine (TMB, Zymed, California, USA) were used for the visualization in a dark room. The reaction was stopped with 50 μL/well of 12.5% sulfuric acid and the reading was carried out at 450 nm using a Labsystems iEMS Reader MF plate reader used with the Ascent 2.6 software (Thermo LabSystems, Cergy Pontoise, France).

The optimum conditions for the ELISA were defined by testing serum samples at dilutions of 1/10, 1/100 and 1/300, and amounts of L20h-Ts3 protein of 50 ng, 250 ng, 500 ng and 1 μg per well. The results obtained were then analyzed by means of a Wilcoxon-Mann-Whitney test. Thus, the greatest difference between the values of the positive samples and the values of the negative samples was observed for a dilution of 1/10 of the sera and 250 ng of L20h-Ts3 protein. These conditions were therefore used during the subsequent ELISAs.

These conditions were therefore used for the remainder of the tests. The diagnostic threshold was determined using negative reference sera. The calculation is based on the use of the formula defined by the Office International des Epizooties [World Organization for Animal Health] (Manual of diagnostic tests and vaccines for land animals, 6th ed., 2008, chapter 2.01.6), corresponding to the mean of the ODs measured at 450 nm to which 3 times the standard deviation is added.

The results are illustrated by FIGS. 5 to 13.

Figure 5:
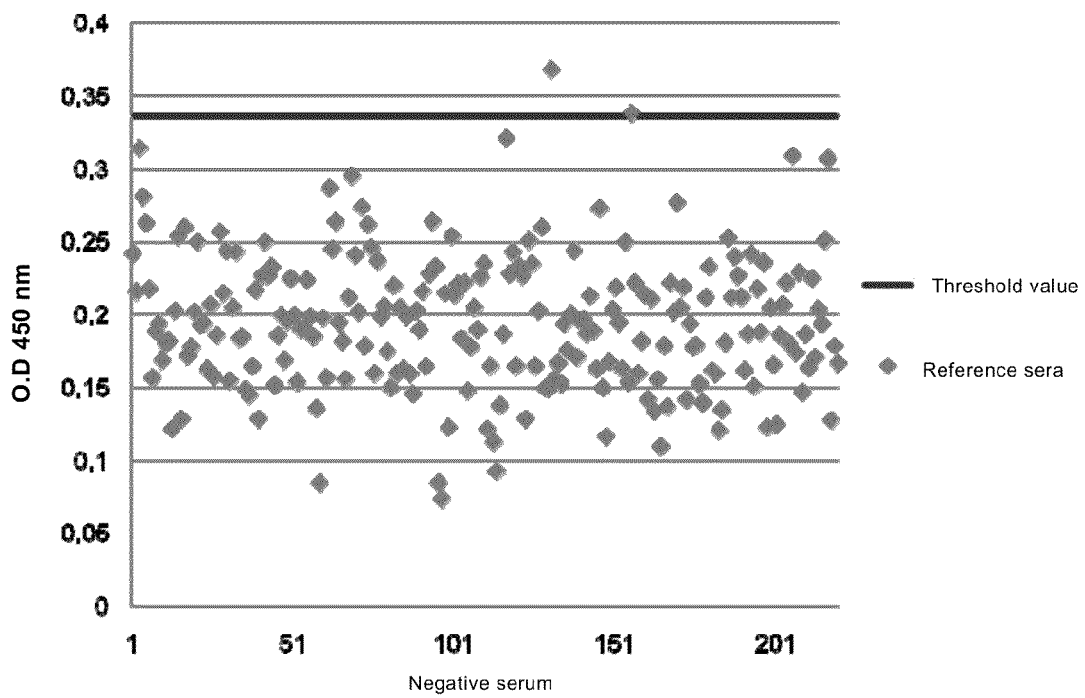
FIG. 5 shows the optical density values measured on 220 negative reference sera.

FIG. 5 represents the optical density values measured on 220 negative reference sera. The diagnostic threshold established on the basis of these measurements is 0.33 OD unit.

Figure 6:
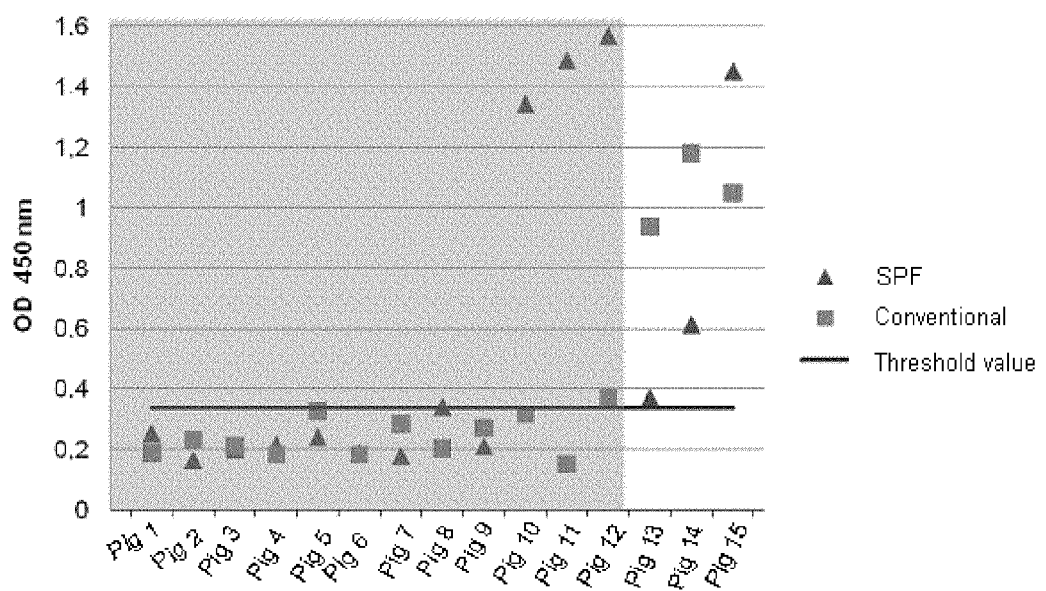
FIG. 6 shows the optical density values measured with sera of SPF pigs or of pigs from a conventional farm.

FIG. 6 represents the optical density values measured with sera of SPF pigs (▲) or of pigs from a conventional farm (■), infested with 20 000 L1M larvae of *T. spiralis*, for sera collected 5 (pigs 1-3), 12 (pigs 4-6), 15 (pigs 7-9), 20 (pigs 10-12) and 60 (pigs 13-15) days pi. The blind window, during which no detection is possible with the E/S ELISA, is represented in shading.

Figure 7:
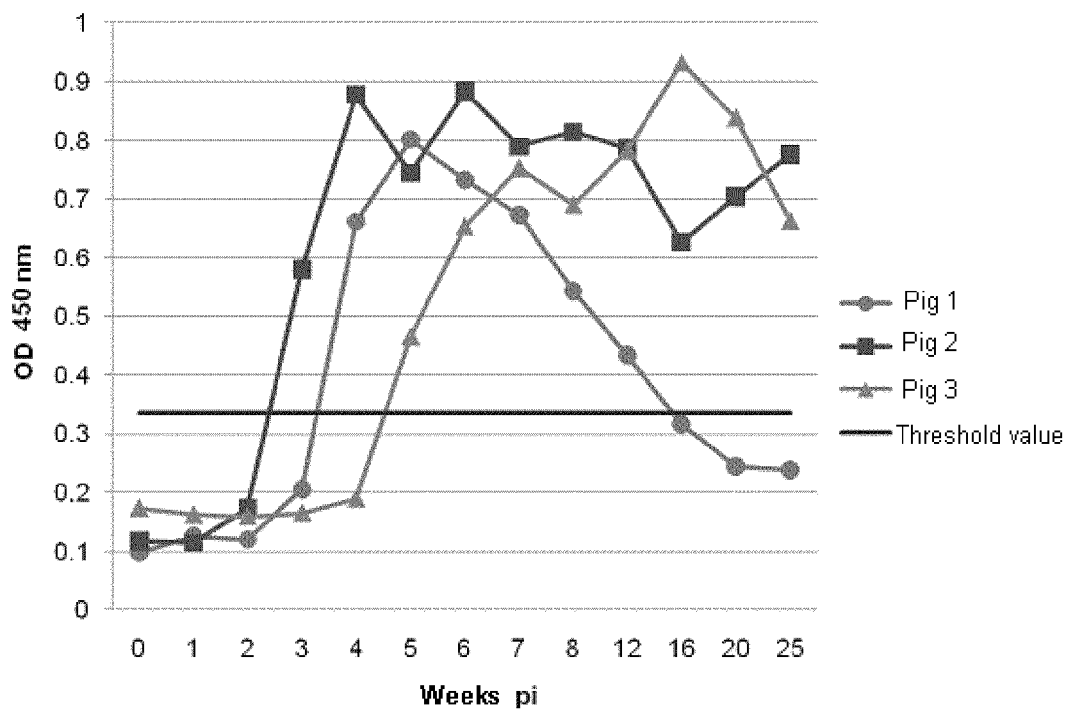
FIG. 7 shows the change in optical density (along the y-axis) during the weeks following infestation (along the x-axis) for the sera of 3 SPF pigs experimentally infested with 20,000 L1M larvae of *T. spiralis* and tested with the L20h-Ts3 antigen.

FIG. 7 represents the change in optical density (along the y-axis) during the weeks following infestation (along the x-axis) for the sera of 3 SPF pigs experimentally infested with 20 000 L1M larvae of *T. spiralis* and tested with the L20h-Ts3 antigen.

Figure 8:
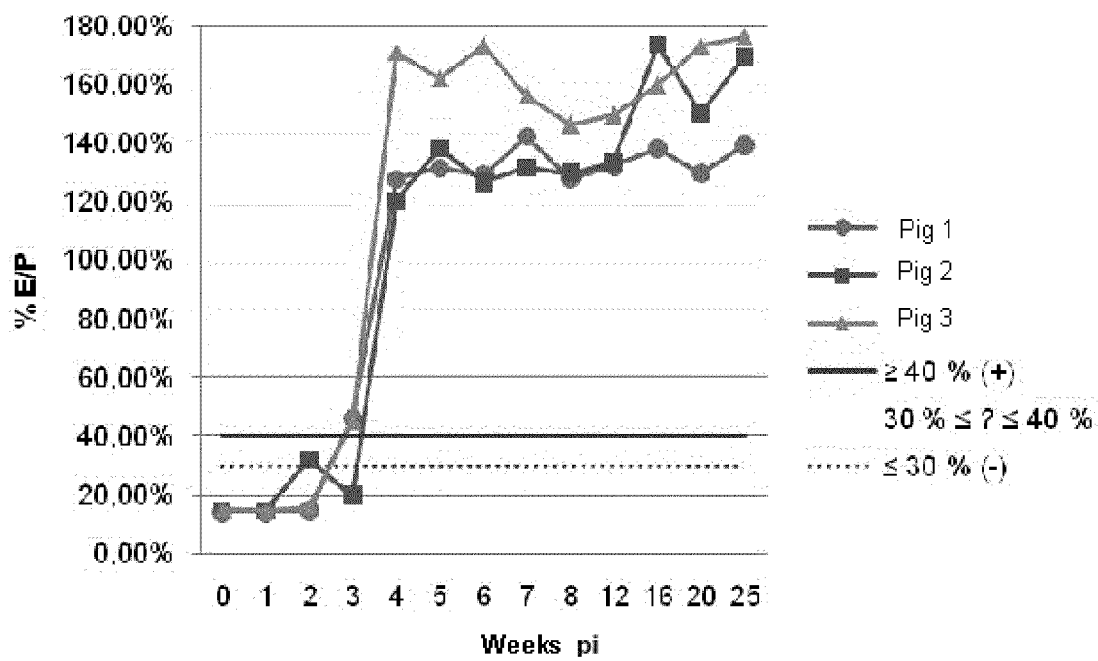
FIG. 8 shows the change in optical density (along the y-axis) during the weeks following infestation (along the x-axis) for the sera of 3 SPF pigs experimentally infested with 20,000 L1M larvae of *T. spiralis* and tested with the E/S antigen.

FIG. 8 represents the change in optical density (along the y-axis) during the weeks following infestation (along the x-axis) for the sera of 3 SPF pigs experimentally infested with 20 000 L1M larvae of *T. spiralis* and tested with the E/S antigen. The % E/P is defined by the following formula: (OD of the test sample)/(mean OD of the positive control sample)× 100.

Figure 9:
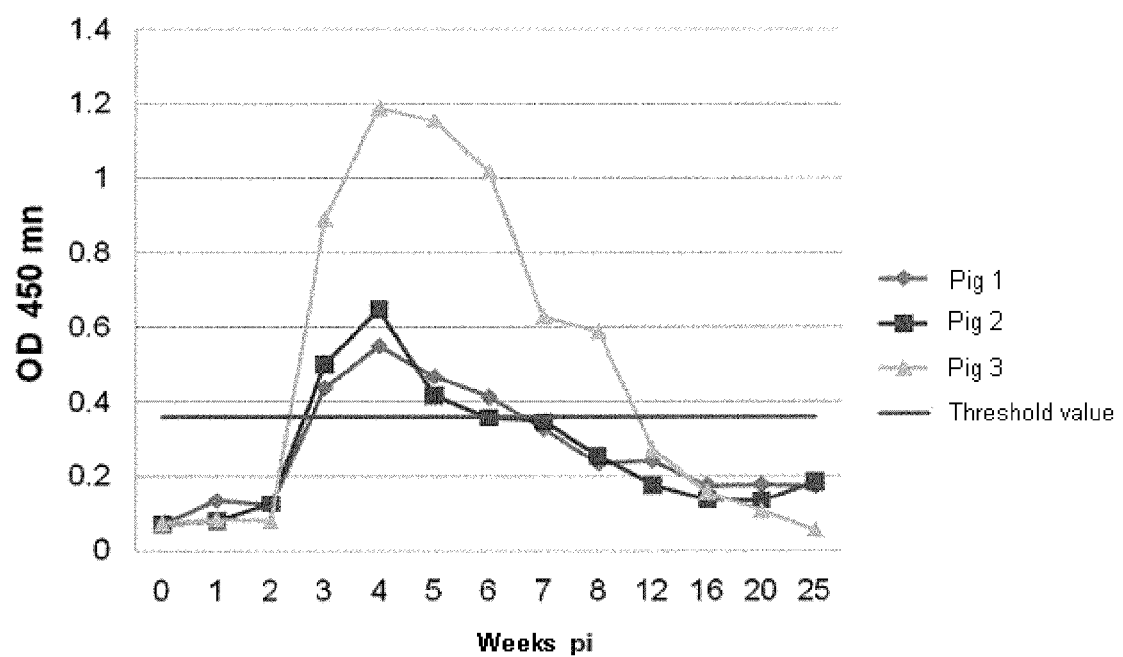
FIG. 9 shows the change in optical density (along the y-axis) during the weeks following infestation (along the x-axis) for the sera of 3 SPF pigs experimentally infested with 20,000 L1M larvae of *T. spiralis* and tested with the NBL1 antigen.

FIG. 9 represents the change in optical density (along the y-axis) during the weeks following infestation (along the x-axis) for the sera of 3 SPF pigs experimentally infested with 20 000 L1M larvae of *T. spiralis* and tested with the NBL1 antigen.

Figure 10:
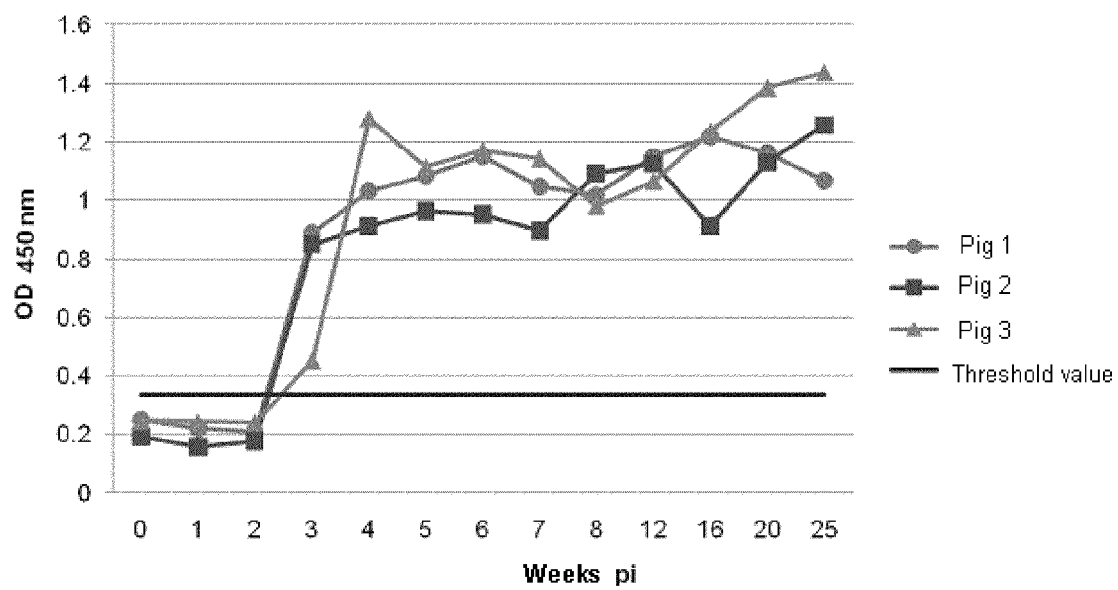
FIG. 10 shows the change in optical density (along the y-axis) during the weeks following infestation (along the x-axis) for the sera of 3 SPF pigs experimentally infested with 20,000 L1M larvae of *T. britovi* and tested with the L20h-Ts3 antigen.

FIG. 10 represents the change in optical density (along the y-axis) during the weeks following infestation (along the x-axis) for the sera of 3 SPF pigs experimentally infested with 20 000 L1M larvae of *T. britovi* and tested with the L20h-Ts3 antigen.

Figure 11:
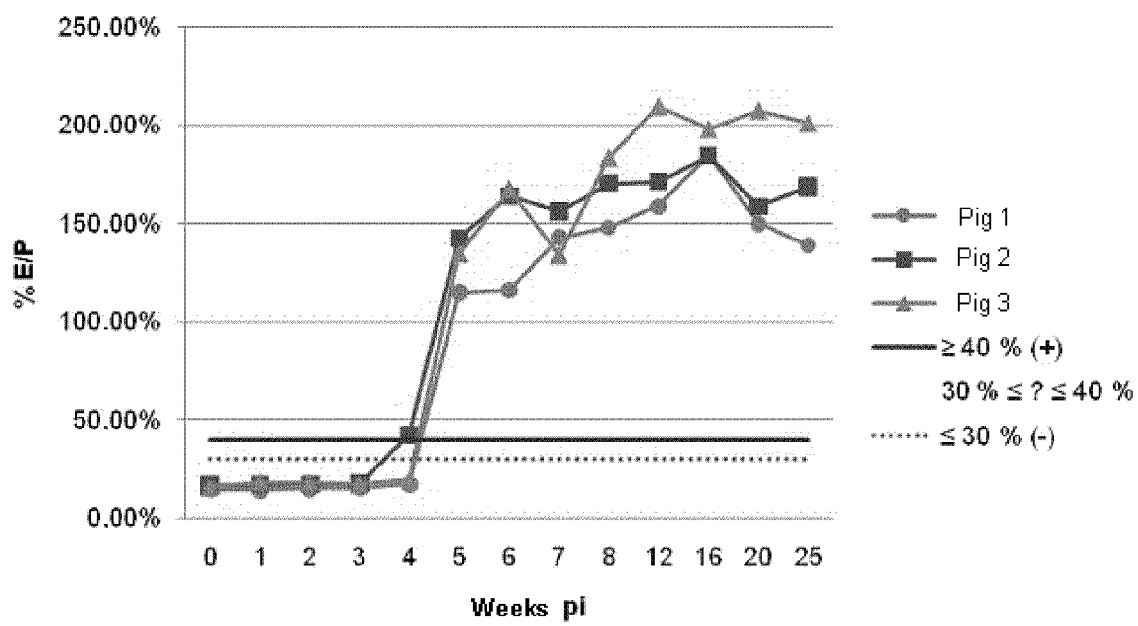
FIG. 11 shows the change in optical density (along the y-axis) during the weeks following infestation (along the x-axis) for the sera of 3 SPF pigs experimentally infested with 20,000 L1M larvae of *T. britovi* and tested with the E/S antigen.

FIG. 11 represents the change in optical density (along the y-axis) during the weeks following infestation (along the x-axis) for the sera of 3 SPF pigs experimentally infested with 20 000 L1M larvae of *T. britovi* and tested with the E/S antigen.

Figure 12:
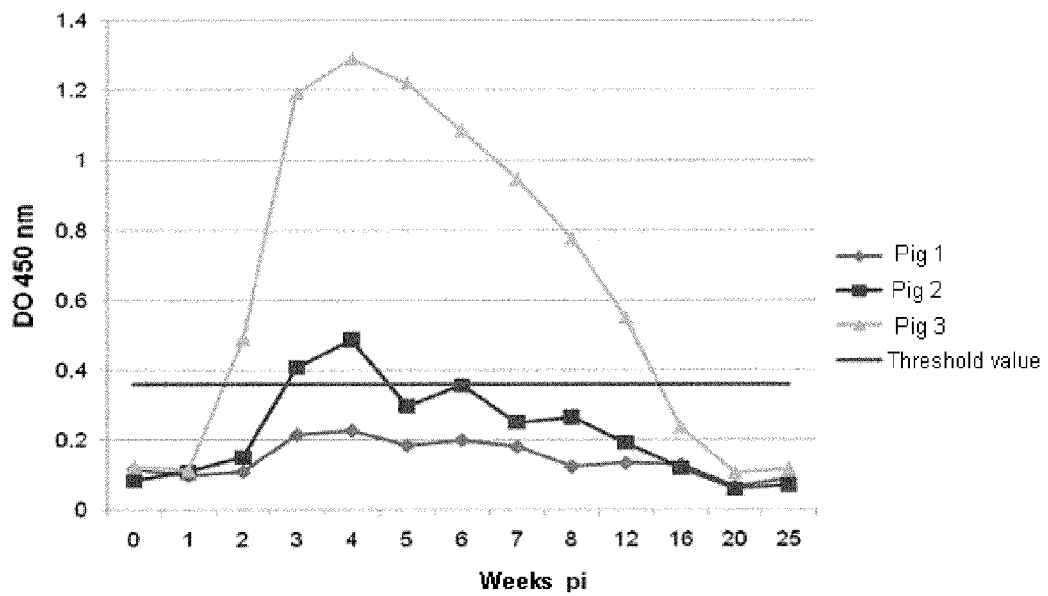
FIG. 12 shows the change in optical density (along the y-axis) during the weeks following infestation (along the x-axis) for the sera of 3 SPF pigs experimentally infested with 20,000 L1M larvae of *T britovi* and tested with the NBL1 antigen.

FIG. 12 represents the change in optical density (along the y-axis) during the weeks following infestation (along the x-axis) for the sera of 3 SPF pigs experimentally infested with 20 000 L1M larvae of *T. britovi* and tested with the NBL1 antigen.

Figure 13:
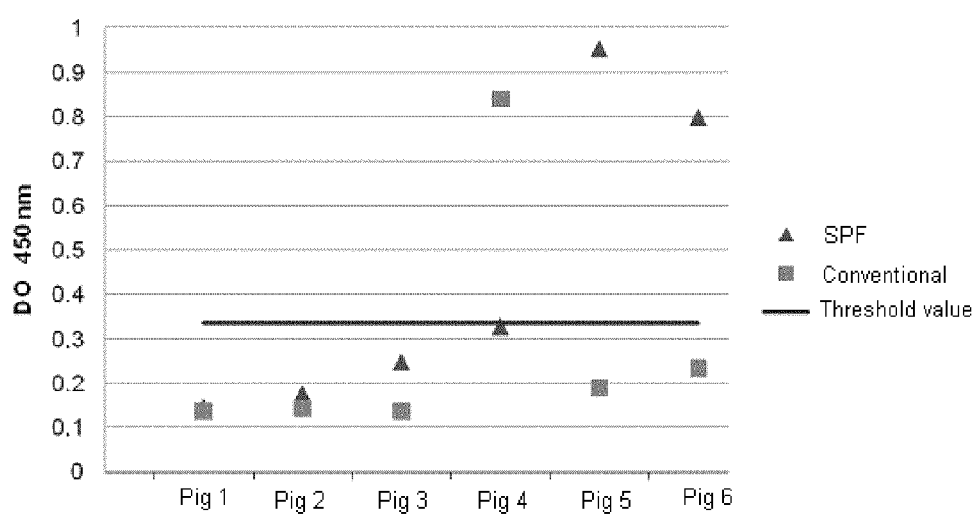
FIG. 13 shows the values of optical density measured with sera of SPF pigs or of pigs from a conventional farm, infested with 200 (pigs 1-3) or 1000 (pigs 4-6) L1M larvae of *T spiralis* and tested with the L20h-Ts3 antigen.

FIG. 13 represents the values of optical density measured with sera of SPF pigs (▲) or of pigs from a conventional farm (■), infested with 200 (pigs 1-3) or 1000 (pigs 4-6) L1M larvae of *T. spiralis* and tested with the L20h-Ts3 antigen.

In the case of pigs experimentally infested with 20 000 L1M of *T. spiralis*, detection with the L20h-Ts3 antigen was possible from 15 days pi for 1/6 pigs (pig 8) and 20 days pi for 4/6 pigs (FIG. 6). As for the E/S ELISA, it did not enable detection of the infection before 25 days. The results obtained were different depending on the health status of the pigs. Specifically, the SPF pigs were detected earlier compared with the conventional pigs.

The seroconversion is accompanied by a profile of humoral responses having high titers and maintained up to 25 weeks pi for 2/3 pigs and up to 12 weeks pi for 1/3 pigs infested with *T. spiralis* (FIG. 7). One pig out of three was detected earlier (1 week earlier) then with the E/S ELISA (FIG. 8). On the same 3 animals, the NBL1 antigen (FIG. 9) enabled detection of anti-*Trichinella* antibodies from 3 weeks pi. On the other hand, a drop in response is observed at 7 weeks pi for 2 of these 3 pigs. For the third pig, the presence of anti-*Trichinella* antibodies is no longer detected after 12 weeks.

In the case of pigs experimentally infested with 20 000 L1M of *T. britovi*, the seroconversion was observed one to two weeks earlier with the L20h-Ts3 antigen than with the E/S ELISA (FIGS. 10 and 11), with measured ODs that were high from 3 weeks pi and maintained up to 25 weeks pi for the three pigs tested. On the same 3 animals, the NBL1 antigen (FIG. 12) enabled the detection of anti-*Trichinella* antibodies in the serum of one of the pigs from 2 weeks pi and up to 16 weeks pi. The presence of anti-*Trichinella* antibodies was detected in the serum of a second pig only in the third and fourth weeks pi. Finally, no anti-*Trichinella* antibody was detected in the serum of the third pig.

Furthermore, 3/6 pigs with a moderate infesting dose (1000 L1M, *T. spiralis*) were detected at 60 days pi with the L20h-Ts3 antigen (FIG. 13). Once again, the results obtained were dependent on the health status of the pigs. Specifically, 2/3 SPF pigs and 1/3 conventional pigs were detected. The pigs infested with a low infesting dose (200 L1M, *T. spiralis*) were not detected at 60 days pi.

The invention claimed is:

1. An in vitro method of detecting anti-*Trichinella* antibodies infestation in a biological sample from a subject to be tested for said antibodies, comprising:

bringing said biological sample into contact with a reagent composition comprising an antigenic polypeptide which binds to an anti-*Trichinella* antibody resulting from *Trichinella* infestation, wherein the antigenic polypeptide comprises SEQ ID NO: 2, under conditions which allow the formation of an antigen/antibody complex with the anti-*Trichinella* antibodies possibly present in said sample; and detecting the antigen/antibody complex possibly formed.

2. The method as claimed in claim 1, wherein the reagent composition is further comprises buffers and reagents suitable for making up a reaction medium which allows the formation of an antigen/antibody complex.

3. The method as claimed in claim 1, wherein said antigenic polypeptide is immobilized on a solid support.

4. The method as claimed in claim 1, wherein the reagent composition further comprises a polypeptide comprising amino acids 21-67 of SEQ ID NO: 4.

5. The method as claimed in claim 1, wherein the antigenic polypeptide is fused to one or more heterologous polypeptide(s).

* * * * *

SEQUENCE LISTING

```
<160> NUMBER OF SEQ ID NOS: 4

<210> SEQ ID NO 1
<211> LENGTH: 398
<212> TYPE: DNA
<213> ORGANISM: Trichinella spiralis
<220> FEATURE:
<221> NAME/KEY: CDS
<222> LOCATION: (34)..(351)

<400> SEQUENCE: 1
gggtcagttt tagcagcttt tatcttcttt ttc atg gca gtt atg cct gaa atc      54
                                    Met Ala Val Met Pro Glu Ile
                                    1               5 aat gcg gat ttg agt cca ttg gaa gaa gcc caa agt tac ata tac caa      102
Asn Ala Asp Leu Ser Pro Leu Glu Glu Ala Gln Ser Tyr Ile Tyr Gln
        10                  15                  20 tct gat ttg caa agc ggt aaa ggt cat ttc cgc aga gtt ctc gat ata      150
Ser Asp Leu Gln Ser Gly Lys Gly His Phe Arg Arg Val Leu Asp Ile
    25                  30                  35 agc gat gtc gac aca agt gac gga tta tcc tta acg ata gac gct ctt      198
```

```
Ser Asp Val Asp Thr Ser Asp Gly Leu Ser Leu Thr Ile Asp Ala Leu
 40              45                  50                  55 cca act aca tgt cct gtg tca tca gaa atg act caa gat caa gtg tat       246
Pro Thr Thr Cys Pro Val Ser Ser Glu Met Thr Gln Asp Gln Val Tyr
                 60                  65                  70 tca gat gag tgc ccc gtc acc aga gag gaa tat gac gaa ata gaa tgc       294
Ser Asp Glu Cys Pro Val Thr Arg Glu Glu Tyr Asp Glu Ile Glu Cys
             75                  80                  85 cat ttg aag ctt gac cat tct aaa act ggc caa att gaa tgt aca tat       342
His Leu Lys Leu Asp His Ser Lys Thr Gly Gln Ile Glu Cys Thr Tyr
         90                  95                 100 tat gga cat taaactatga gaataaagtg atttaatgaa aaaaaaaaaa aaaaaa        398
Tyr Gly His
        105

<210> SEQ ID NO 2
<211> LENGTH: 106
<212> TYPE: PRT
<213> ORGANISM: Trichinella spiralis

<400> SEQUENCE: 2

Met Ala Val Met Pro Glu Ile Asn Ala Asp Leu Ser Pro Leu Glu Glu
  1               5                  10                  15

Ala Gln Ser Tyr Ile Tyr Gln Ser Asp Leu Gln Ser Gly Lys Gly His
             20                  25                  30

Phe Arg Arg Val Leu Asp Ile Ser Asp Val Asp Thr Ser Asp Gly Leu
         35                  40                  45

Ser Leu Thr Ile Asp Ala Leu Pro Thr Thr Cys Pro Val Ser Ser Glu
 50                  55                  60

Met Thr Gln Asp Gln Val Tyr Ser Asp Glu Cys Pro Val Thr Arg Glu
 65                  70                  75                  80

Glu Tyr Asp Glu Ile Glu Cys His Leu Lys Leu Asp His Ser Lys Thr
             85                  90                  95

Gly Gln Ile Glu Cys Thr Tyr Tyr Gly His
            100                 105

<210> SEQ ID NO 3
<211> LENGTH: 339
<212> TYPE: DNA
<213> ORGANISM: Trichinella spiralis
<220> FEATURE:
<221> NAME/KEY: CDS
<222> LOCATION: (1)..(201)

<400> SEQUENCE: 3 atg ttc atc acg ttt atc ttt ctt gct aac ata ctg ctt ctt gtg caa        48
Met Phe Ile Thr Phe Ile Phe Leu Ala Asn Ile Leu Leu Leu Val Gln
  1               5                  10                  15 cca tcg gaa gca tat cgt ggt cac acc aac gat gaa att cga ttg atg        96
Pro Ser Glu Ala Tyr Arg Gly His Thr Asn Asp Glu Ile Arg Leu Met
             20                  25                  30 gat gag tgt agc gat gaa cca tac ata cga gaa cac ttg ggg gaa gat       144
Asp Glu Cys Ser Asp Glu Pro Tyr Ile Arg Glu His Leu Gly Glu Asp
         35                  40                  45 gat tat atg agt tta att gat gcg tgc gtt gaa gaa cga ctt gga cga       192
Asp Tyr Met Ser Leu Ile Asp Ala Cys Val Glu Glu Arg Leu Gly Arg
 50                  55                  60 aga gtt gca tgaagaatat aagaaaagct atcaagaatt gttcattttc               241
Arg Val Ala
 65
```

```
aagcgacaat tttatttatg aaatgaattt attgaaaaat gaaaatctgt tacagtattc    301
gtaataaata gctatgcagt aaaaaaaaaa aaaaaaa                             339
```

<210> SEQ ID NO 4
<211> LENGTH: 67
<212> TYPE: PRT
<213> ORGANISM: Trichinella spiralis

<400> SEQUENCE: 4

```
Met Phe Ile Thr Phe Ile Phe Leu Ala Asn Ile Leu Leu Leu Val Gln
1               5                   10                  15

Pro Ser Glu Ala Tyr Arg Gly His Thr Asn Asp Glu Ile Arg Leu Met
            20                  25                  30

Asp Glu Cys Ser Asp Glu Pro Tyr Ile Arg Glu His Leu Gly Glu Asp
        35                  40                  45

Asp Tyr Met Ser Leu Ile Asp Ala Cys Val Glu Glu Arg Leu Gly Arg
    50                  55                  60

Arg Val Ala
65
```